US00PP20880P2

(12) United States Plant Patent
Jandrew

(10) Patent No.: US PP20,880 P2
(45) Date of Patent: Mar. 23, 2010

(54) *IPOMOEA* PLANT NAMED 'SEKI BLAPALM'
(50) Latin Name: *Ipomoea batatas* (L.) Lam
Varietal Denomination: Seki Blapalm

(75) Inventor: Jason Jandrew, Gilroy, CA (US)
(73) Assignee: Syngenta Crop Protection AG, Basel (CH)

( * ) Notice: Subject to any disclaimer, the term of this patent is extended or adjusted under 35 U.S.C. 154(b) by 0 days.
(21) Appl. No.: 12/316,290
(22) Filed: Dec. 11, 2008
(51) Int. Cl.
*A01H 5/00* (2006.01)
(52) U.S. Cl. ..... Plt./263.1
(58) Field of Classification Search ..... Plt./263.1, Plt./258
See application file for complete search history.
*Primary Examiner*—Kent L Bell
(74) *Attorney, Agent, or Firm*—S. Matthew Edwards

(57) ABSTRACT

A new *Ipomoea* plant named 'Seki Blapalm' particularly distinguished by compact and mounding plant habit that becomes more outwardly trailing with age, vigorous, freely branching with dense foliage, and very dark, almost black palmately lobed foliage, with soft purple-violet and white flowers.

1 Drawing Sheet

Latin name of the genus and species of the plant claimed: *Ipomoea batatas* (L.) Lam.

Varietal denomination: 'Seki Blapalm'.

BACKGROUND OF THE NEW PLANT

The present invention comprises a new *Ipomoea*, botanically known as *Ipomoea batatas* (L.) Lam, and commonly known as Ornamental Sweet Potato, and hereinafter referred to by the variety name 'Seki Blapalm.' These plants are grown, not for their flowers, but for their foliage and plant habit characteristics. These plants flower very rarely and then only under strict short day lengths. Each flower is ephemeral, in that it only lasts up to 24 hours, and blooms mostly through the night and early morning hours.

'Seki Blapalm' is a product of a planned breeding program. The new cultivar 'Seki Blapalm' has a compact and mounding plant habit that becomes more outwardly trailing with age, vigorous, freely branching with dense foliage, and very dark, almost black palmately lobed foliage, with soft purple-violet and white flowers.

'Seki Blapalm' originated from an open pollination in a controlled breeding program in Gilroy, Calif. USA. The female parent was 'Sweet Caroline Purple' (U.S. Plant Pat. No. 14,912). 'Sweet Caroline Purple' has a less compact plant habit, shorter petioles and lighter colored foliage than 'Seki Blapalm.' The male parent of 'Seki Blapalm' was unknown.

'Seki Blapalm' was selected as one flowering plant within the progeny of the stated cross in March 2007, in a controlled environment in Gilroy, Calif. USA. The pollination took place in July 2006 and the seed sown in December 2006.

The first act of asexual reproduction of 'Seki Blapalm' was accomplished when vegetative cuttings were taken from the initial selection in the March 2007 in a controlled environment in Gilroy, Calif. USA.

Horticultural examination of plants grown from cuttings of the plant initiated in March 2007 in Gilroy, Calif. USA, and continuing thereafter, has demonstrated that the combination of characteristics as herein disclosed for 'Seki Blapalm' are firmly fixed and are retained through successive generations of asexual reproduction.

'Seki Blapalm' has not been observed under all possible environmental conditions. The phenotype may vary significantly with variations in environment such as temperature, light intensity and day length.

A Plant Breeder's Right for this cultivar was applied for in Canada on Dec. 24, 2007. 'Seki Blapalm' has not been made publicly available more than one year prior to the filing of this application.

DESCRIPTION OF DRAWING

The accompanying photographic drawing shows typical foliage and plant habit characteristics of 'Seki Blapalm' with colors being as true as possible with an illustration of this type. The photographic drawing shows 3 potted plants of the new variety growing in a 14 inch container. These plants were grown and photographed in Gilroy, Calif. USA in the summer of 2008.

DETAILED BOTANICAL DESCRIPTION

The measurements were taken in October 2008 in Gilroy, Calif. USA on plants that were growing in 6 inch pots in a greenhouse. Culture of these plants started in about August 2008, when they came from sterile tissue culture tubes after laboratory micropropagation.

Color Chart used: Royal Horticultural Society Colour Chart (R.H.S.) 2001

BRIEF SUMMARY OF INVENTION

The following observations, measurements, and comparisons describe plants grown in Gilroy, Calif. USA. The following traits have been repeatedly observed and are determined to be basic characteristics of the new variety. The combination of these characteristics distinguishes this *Ipomoea* as a new and distinct variety.

TABLE 1

DIFFERENCES BETWEEN THE NEW VARIETY 'SEKI BLAPALM' AND A SIMILAR VARIETY

| | 'Seki Blapalm' | 'Sweet Caroline Purple' (U.S. Plant Pat. No. 14,912) |
|---|---|---|
| Petiole size | Longer | Shorter |
| Foliage size/color | Larger/darker | Smaller/lighter |
| Throat color | Lighter | Darker |
| Sepal size | Shorter | Longer |

Plant:

*Form, growth and habit.*—Compact and mounding plant habit that becomes more outwardly trailing with age, vigorous, freely branching with dense foliage.

*Height.*—17–22 cm.

*Width.*—35–42 cm.

Roots/tubers:

*Type.*—At the age of these plants used for the descriptive data, there were no real tubers forming. The roots themselves are thick, fleshy and cream to white.

Foliage:

*Type.*—Alternate, simple.

*Immature, leaf color, upper surface.*—RHS 144A, mottled with slight patches of RHS 144B.

*Lower surface.*—Closest to RHS 146C.

*Mature, leaf color, upper surface.*—RHS N189A but somewhat darker, overlaid with anthocyanins closest to RHS N186A.

*Lower surface.*—Closest to RHS 146C.

*Color of veins, upper surface.*—RHS 187A.

*Color of veins, lower surface.*—RHS 187A.

*Length.*—13.6–15 cm.

*Width.*—15–17 cm.

*Shape.*—Roughly deltoid; palmately, 5 lobed.

*Base shape.*—Heavily cordate to sagittate.

*Apex shape.*—Apiculate.

*Margin.*—Entire.

*Texture.*—Hirsute on the margins of both surfaces.

*Color of veins, upper surface.*—RHS 187A.

*Color of veins, lower surface.*—RHS 187A.

*Petioles color.*—RHS 187A.

*Petioles length.*—13.5–14.5 cm.

*Diameter of petiole.*—0.3–0.4 cm.

*Texture.*—Glabrous.

Stem:

*Color of stem.*—RHS 187A.

*Length of stem.*—5.7–6.5 cm.

*Diameter.*—0.3–0.5 cm.

*Length of internodes.*—0.5–1.0 cm.

*Texture.*—Glabrous.

Inflorescence:

*Type.*—Ephemeral; rarely see flowers. Flowers only under very strict short day lengths.

*Fragrance.*—None.

*Color of peduncle.*—RHS 187A but slightly lighter.

*Length of peduncle.*—2–4 cm.

*Peduncle diameter.*—0.2 cm.

*Texture.*—Glabrous.

Corolla:

*Form.*—Single trumpet-shaped flowers arise from leaf axils comprised of 5 petals fused at the corolla length and base.

*Flower diameter.*—3.5–3.7 cm.

*Flower depth.*—3.5–3.6 cm.

*Color of petals, upper surface.*—RHS 65D; RHS N155C margins; veins RHS N77B.

*Color of petals, lower surface.*—RHS 186C and 186D; RHS N155B margins.

*Length of petals.*—1.3–1.5 cm.

*Width of petals.*—1.2–1.3 cm.

*Petal shape.*—Obcordate.

*Apex shape.*—Acute.

*Margin.*—Entire.

*Petal texture.*—Papillose on upper surface and glabrous under.

*Corolla color inner surface.*—RHS N81D ground color; RHS N80B basally; RHS N79B veining that fades to RHS N77B at petal lobes.

*Outer surface.*—RHS 186C and 186D, slightly striated and suffused together.

*Corolla diameter at flare.*—1.5–1.6 cm.

Bud (just before opening):

*Color.*—RHS 65C.

*Length.*—2.1–2.2 cm.

*Width.*—0.5–0.7 cm.

*Shape.*—Orbicular.

*Calyx.*—5 sepals fused at the base.

*Color of sepals, inner surface.*—Closest to RHS N186C.

*Outer surface.*—Closest to RHS 145A, overlaid with anthocyanins of about RHS N186A to N186B.

*Length of sepals.*—0.7–0.8 cm.

*Width of sepals.*—0.2–0.3 cm.

*Sepal shape.*—Lanceolate.

*Apex shape.*—Acute.

*Margins.*—Entire.

*Texture.*—Slightly pubescent on the outer surface and glabrous on the inner surface.

Reproductive organs:

*Pistil.*—1.

*Length.*—1.3–1.5 cm.

*Style color.*—RHS N155B but whiter.

*Style length.*—1.2–1.3 cm.

*Stigma color.*—RHS N155B but whiter.

*Stamens.*—5.

*Color of filaments.*—RHS N155B but whiter.

*Length filaments.*—0.4 cm.

*Anther color.*—RHS 155C.

*Length of anthers.*—0.1–0.2 cm.

*Color of pollen.*—RHS 155A.

*Pollen amount.*—Scarce.

*Fertility/seed set.*—Not observed on this hybrid.

Disease/pest resistance: Disease resistance or susceptibility has not been observed on this hybrid.

What is claimed is:

1. A new and distinct variety of *Ipomoea* plant named 'Seki Blapalm,' substantially as illustrated and described herein.

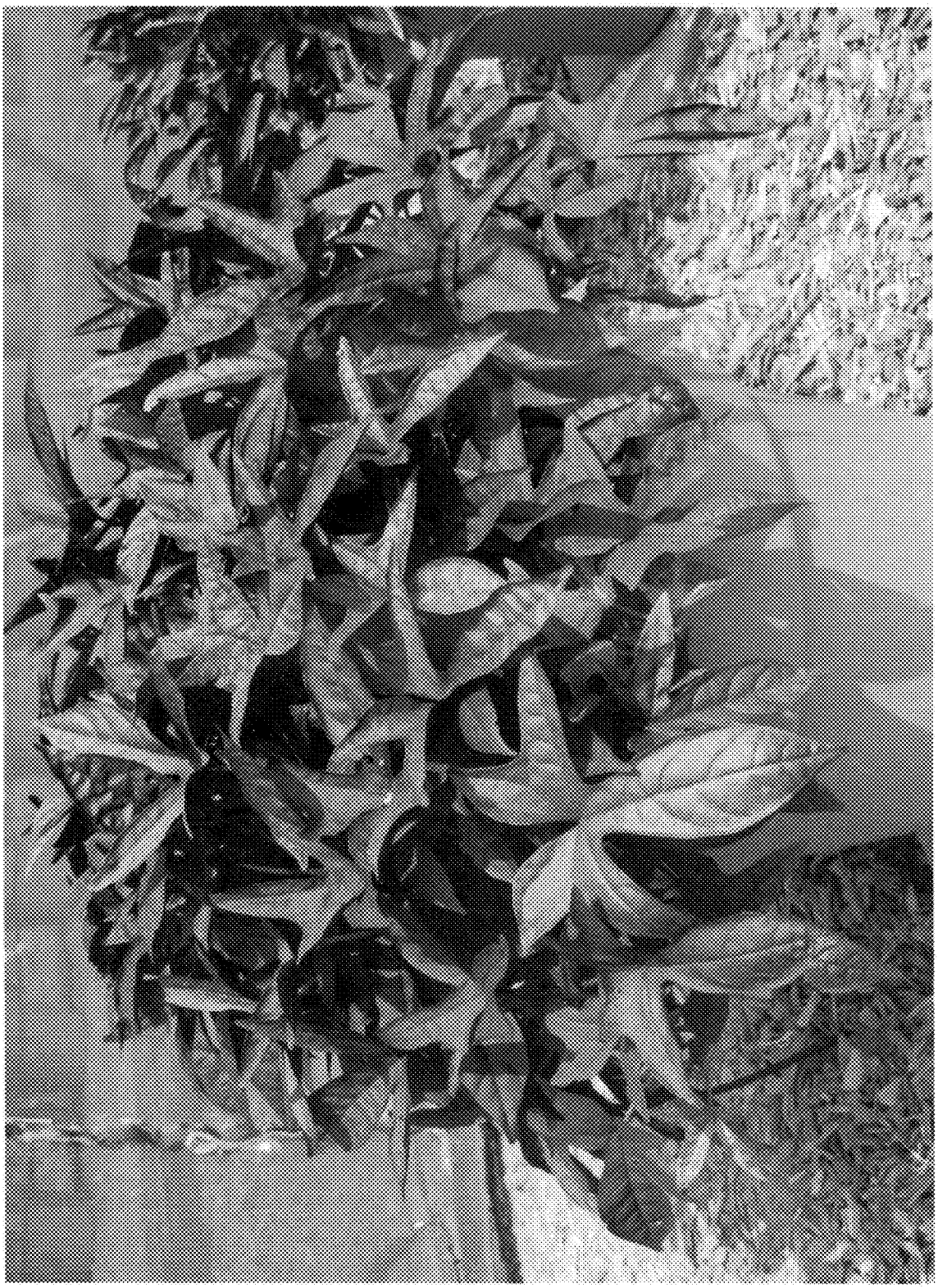

* * * * *